(12) United States Patent
Napoletano et al.

(10) Patent No.: US 7,834,040 B2
(45) Date of Patent: Nov. 16, 2010

(54) ISOXAZOLIC DERIVATIVE TO RELIEVE NEUROPATHIC PAIN

(75) Inventors: Mauro Napoletano, Milan (IT); Ermanno Moriggi, Busto Arsizio (IT)

(73) Assignee: Zambon S.p.A., Bresso (IT)

( * ) Notice: Subject to any disclaimer, the term of this patent is extended or adjusted under 35 U.S.C. 154(b) by 667 days.

(21) Appl. No.: 11/718,935

(22) PCT Filed: Nov. 14, 2005

(86) PCT No.: PCT/EP2005/055940

§ 371 (c)(1),
(2), (4) Date: May 9, 2007

(87) PCT Pub. No.: WO2006/053860

PCT Pub. Date: May 26, 2006

(65) Prior Publication Data

US 2008/0108679 A1     May 8, 2008

(30) Foreign Application Priority Data

Nov. 16, 2004  (IT)  .......................... MI2004A2187

(51) Int. Cl.
*A61K 31/42* (2006.01)
*C07D 261/08* (2006.01)
*A61P 25/02* (2006.01)

(52) U.S. Cl. ...................................... 514/378; 548/248

(58) Field of Classification Search ....................... None
See application file for complete search history.

(56) References Cited

U.S. PATENT DOCUMENTS 4,985,428 A * 1/1991 Carenzi et al. ................. 514/18

FOREIGN PATENT DOCUMENTS

WO    WO 88/09330    12/1988

OTHER PUBLICATIONS

Rashid et al, The Journal of pharmacology and experimental therapeutics, vol. 303, 2002, pp. 226-231.*
S. Ricciardi, et al., Behavioural and Biochemical Effects of a New. . . , J. Drug Dev., vol. 6, No. 4, pp. 159-170, 1994.
S. Ricciardi, et al., Z-4105, Drugs of the Future, vol. 20, No. 6, pp. 584-586, 1995.

* cited by examiner

*Primary Examiner*—Kamal A Saeed
(74) *Attorney, Agent, or Firm*—Lucas & Mercanti, LLP

(57) ABSTRACT

The present invention relates to new pharmaceutical uses of an isoxazolic derivative or a pharmaceutically acceptable salt thereof in the preparation of a medicament useful for treating the neuropathic pain.

5 Claims, No Drawings

ISOXAZOLIC DERIVATIVE TO RELIEVE NEUROPATHIC PAIN

The present invention relates to new pharmaceutical uses of an isoxazolic derivative. In particular, the present invention relates to an isoxazolic derivative of formula (I)

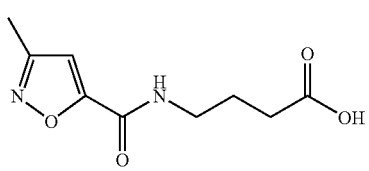

(I)

or a pharmaceutically acceptable salt thereof, for use in the preparation of a medicament for treating the neuropathic pain.

The compound of formula (I) is also known as Z 4105.

The pain is usually defined as an unpleasant sensorial and emotional experience associated to real or potential tissue damage and described in terms of such damage. In particular, the neuropathic pain is due to a damage of the central and/or peripheral nervous system. It is namely an anatomic and/or functional anomaly of the mechanism signaling pain, without the activation of nociceptors.

In Italy it is estimated that about 6% of the population in some moment of the life suffers from episodic or constant neuropathic pain. We are speaking about 4 million people, ⅔ million thereof suffer there from in a chronic way.

The neuropathic pain appears in a variety of forms comprising the spontaneous pain (painful sensation without an outer stimulation), allodinia (painful sensation in response to a usually innocuous stimulation) and iperalgesia (strong painful sensation in response to a little painful stimulus).

The symptoms characterizing this pain usually vary from patient to patient, but generally they are felt as sensations of lancinating or continuous sting, tingle, needles' pricks, numbness of the limbs and/or electric shocks.

The most frequent causes of the neuropathic pain can include, for example, diseases such as diabetes, herpes zoster, paralytic stroke, rheumatoid arthritis, lumbosciatica and facial neuralgia. The nervous lesion causing the onset of the neuropathic pain can be the consequence of various surgical operations, such as for example saphenectomy, or of traumas such as, for example, car accidents. Furthermore, the neuropathic pain can appear in concomitance with nervous degenerative diseases, bone degenerative diseases, metabolic diseases, cancer, infections, inflammatory states, anti-cancer radiotherapy and chemotherapy.

The neuropathic pain is unlikely to be treated and it currently represents one of the most frustrating problems of the antalgic therapy. Classic analgesics are often ineffective, including morphine itself. Often one resorts to palliative pharmacological therapies with antidepressants or anticonvulsants or to more invasive techniques such as block anesthesia, neurostimulations or to surgical operations, but unfortunately specific resolutive treatments do not yet exist.

Since the neuropathic pain is a therapeutic area thereto an adequate pharmacological response has not yet given, there is a continuous search for new drugs more effective in relieving this pathology.

Recent studies suggesting the existence of relationships between the phenomena connected to memory and learning and the chronic pain, they have given the cue for using nootropic compounds for treating the neuropathic pain.

In line with this tendency, the patent application US 2004/0063776 describes the use of pyrrolidonic derivatives comprising known nootropic compounds, such as nefiracetam and oxiracetam, known as preferred compounds for the treatment and/or prophylaxis of the neuropathic pain.

Upon expanding on this aspect, Rashid et al. have demonstrated that, whereas the nootropic drug nefiracetam has a powerful analgesic effect, other nootropes similar to nefiracetam such as piracetam, oxiracetam and levitiracetam, do not produce significant analgesic effects with respect to the neuropathic pain (Journal of Pharmacology and Experimental Therapeutics 303:226-231, 2002).

Subsequently Scapecchi et al., upon detecting as known nootropes belonging to chemical series very similar in structure have conflicting behaviors when tested in the neuropathic pain, come to the conclusion that the mechanism of action of compounds active in the neuropathic pain does not seem to be correlated to the mechanism determining the cognition enhancing (Bioorg. Med. Chem. 12:71-85, 2004).

The present inventors have found that the compound of formula (I) as defined above, whose activity as nootrope is known (see Journal of Drug Development 6(4):159-170, 1994), is effective in the treatment of the neuropathic pain.

This result, apart from being new, can be considered as the product of the inventive effort of the present inventors, as it is not obvious thinking that a nootropic compound is also effective in treating the neuropathic pain in view of the teachings of Rashid and Scapecchi who underline the great variability in the behavior of nootropes, even very similar in structure, in treating the neuropathic pain.

Therefore, a first object of the present invention is the isoxazolic derivative of formula (I)

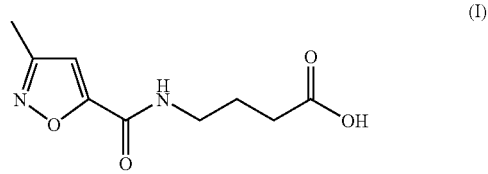

(I)

or a pharmaceutically acceptable salt thereof, for use in the preparation of a medicament for treating the neuropathic pain.

Examples of pharmaceutically acceptable salts of the compound of formula (I) are salts of pharmaceutically acceptable organic and inorganic bases such as, for example, sodium, calcium, magnesium or potassium hydroxide, ammonium, lysine, arginine, cysteine, 2-amino-2-hydroxymethyl-1,3-propanediol, meglumine, piperazine, diethylamine, benzathine and 4-phenylcycloesylamine.

The compound of formula (I) and the pharmaceutically acceptable salts thereof can be prepared, for example, by following the procedure described in the International patent application WO 88/09330.

According to the present invention the term "to treat" or "treatment" comprises the prophylaxis before the onset, the improvement and/or the elimination of the neuropathic pain once it has arisen. In the prophylactic treatment, a compound according to the invention can be administered to a subject at risk of developing the neuropathic pain. In the therapeutic treatment, a compound according to the invention can be administered to a subject experiencing the neuropathic pain.

The therapeutically effective amounts of a compound according to the invention depend upon several factors such as age, the patient's general physiological conditions, the individual response to therapy, the administration route and the utilized pharmaceutical composition. However, the therapeutical doses are generally comprised between 1 mg and about 3000 mg, preferably between about 30 mg and about 2000 mg, daily, divided into one or more administrations.

The compounds of the present invention for the use in therapy and/or in the prophylaxis of the pathology indicated above can be used in a pharmaceutical form suitable for the oral, rectal, sublingual, parental, topic, transdermic or inhalant route. The preferred administration route of the compounds according to the invention is the oral route.

A second object of the present invention relates to a pharmaceutical composition comprising, as active compound, the compound of formula (I) as defined above or a pharmaceutically acceptable salt thereof and at least a pharmaceutically acceptable excipient.

According to the present invention, the compound of formula (I) or a pharmaceutically acceptable salt thereof optionally can be administered in combination with another or more compounds effective in treating the neuropathic pain chosen among, for examples, anticonvulsants (for example, gabapentin, carbamazepine, topiramate and phenytoin), three-cycle anti-depressant drugs (for example amitriptyline, clomipramine, imipramine and nortriptyline), non-steroid anti-inflammatory drugs (for example, ibuprofen, naproxen, diclofenac, indomethacin and acetylsalicylic acid), opiates (for example, morphine) and inhibitors of the cyclooxigenase-2 enzyme (for example celecoxib, rofecoxib, valdecoxib and parecoxib).

It therefore a further object of the present invention pharmaceutical compounds comprising as an active agent, the compound of formula (I) or a pharmaceutically acceptable salt thereof in combination with at least another compound effective in the treatment of the neuropathic pain and at least a pharmaceutically acceptable excipient.

The pharmaceutical compositions object of the present invention can be liquid suitable for the oral and/or parental administration such as, for example, drops, syrups, injectable solutions ready to use or prepared by diluting a lyophilized product and solid or semi-solid such as tablets, capsules, granulates, powders, pellets, vaginal suppositories, suppository preparations, creams, ointments, gels, unguents; or even solutions, suspensions, emulsions or other forms suitable for the administration by inhalatory and transdermic route.

According to the present invention, under the term excipient it is meant an inactive or inert, and therefore innocuous, component, as it is has no pharmacological action, which is used as carrier or diluent of an active compound. Pharmaceutically acceptable excipients are well known in the art and they comprise, for example, diluents, disgregants, thickeners, dyes, aggregants, lubricants, aromatizing and colouring agents. The excipient or the suitable excipients are selected based upon both the pharmaceutical form, the administration route, the desired release speed and/or the preparation method of the active principle.

The preparation of the pharmaceutical compositions according to the invention is carried out by applying techniques known to the persons skilled in the art.

Packaging units comprising a pharmaceutical composition as defined above together with the instructions for use of said compositions in treating the neuropathic pain are comprised in the present invention as well.

A method for treating the neuropathic pain comprising the administration of a therapeutically effective amount of the compound of formula (I) as defined above or a pharmaceutically acceptable salt thereof is further comprised among the objects of the present invention.

The invention also relates to a method for treating the neuropathic pain comprising the administration of a therapeutically effective amount of the compound of formula (I) as defined above or of a pharmaceutically acceptable salt thereof in combination with at least another compound effective in treating the neuropathic pain chosen among those mentioned above.

The effectiveness of the compound of formula (I) has been tested experimentally in two different models of neuropathic pain caused by chronic constrictive lesion of the sciatic nerve of the rat's hind leg (CCI) and by the ligament of the rat's spinal nerve (SNL), according to the procedure reported in the following experimental part.

Experimental Part

To a group of male rats of Wistar strain a peripheral neuropathy has been induced by means of ligature of the sciatic nerve (CCI) according to the Bennet and Xie model (Pain 33:87-107, 1988).

To a second group of male rats of Wistar strain a peripheral neuropathy has been induced by means of ligature of the spinal nerve according to the modified method described by Kim and Chung and which is constituted by the ligature of two (L5-L6) of the three spinal nerves which form the sciatic nerve (Pain 50:355-363, 1992).

In order to evaluate the neuropathic pain, the development of mechanical allodinia was measured by calculating the average of the pain perception thresholds in the animals' legs in response to mechanical stimuli, following the method described by Chaplan et al. (Journal Neurosci. Method. 53:55-63, 1964).

In the first group of experiments the measurements have been carried out before and 14 days after the ligature of the spinal nerve (CCI). In the second group of experiments the same parameter has been similarly evaluated before and 14 days after the ligature of the spinal nerve (SNL). In both groups, the mechanical allodinia threshold has been measured before (pre-treatment) and 0.5, 1, 2, 4 and 6 hours after treatment by oral route with the compound of formula (I) at doses of 3, 30 and 300 mg/kg.

The compound of formula (I) has reduced in a dose-depending way the mechanical allodinia both in the model CCI and in the model SNL of neuropathic pain; the antiallodinic effect has been found statistically significative already starting from the lower dose of 3 mg/kg in both models. This effect has been detected up to 6 hours after the treatment.

These data confirm that the compound of formula (I), causing a marked reduction in the neuropathic allodinia induced by CCI and SNL, can be effective in controlling the neuropathic pain.

The invention claimed is:

1. A method of treating a patient suffering from neuropathic pain comprising administering an effective amount of isoxazolic derivative of formula (I)

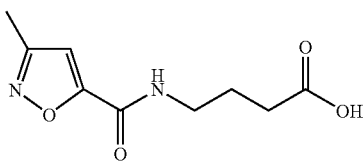 (I)

or a pharmaceutically acceptable salt thereof to a patient in need thereof.

2. A method of treating a patient suffering from neuropathic pain, said method comprising administering a pharmaceutical composition comprising
as an active compound a compound of formula (I) or a pharmaceutically acceptable salt thereof; and
a pharmaceutically acceptable excipient to a patient in need thereof.

3. Method of claim 2, further comprising administering at least a second compound effective in the treatment of neuropathic pain.

4. The method of claim 1, wherein said effective amount is from about 1 mg to about 3000 mg, daily.

5. The method of claim 1, wherein said effective amount is from about 30 mg to about 2000 mg, daily.

* * * * *